United States Patent [19]

Brown, deceased et al.

[11] Patent Number: 4,661,516

[45] Date of Patent: Apr. 28, 1987

[54] DIAMINOCYCLOHEXANE PLATINUM COMPLEXES

[75] Inventors: David B. Brown, deceased, late of Essex Junction, Vt., by Elaine L. Brown, executor; Abdul R. Khokhar, Houston, Tex.; Miles P. Hacker, Williston; John J. McCormack, Burlington, both of Vt.

[73] Assignee: Research Corporation, New York, N.Y.

[21] Appl. No.: 723,107

[22] Filed: Apr. 15, 1985

Related U.S. Application Data

[63] Continuation-in-part of Ser. No. 636,522, Aug. 1, 1984, abandoned, which is a continuation-in-part of Ser. No. 505,965, Jun. 20, 1983, abandoned.

[30] Foreign Application Priority Data

Jun. 18, 1984 [CA] Canada .................. 456842

[51] Int. Cl.$^4$ .......................................... C07F 15/00
[52] U.S. Cl. .................. 514/492; 514/184; 546/2; 546/6; 548/101; 548/106; 549/206; 549/210; 556/137
[58] Field of Search .............. 556/137; 549/210, 206; 514/184, 492; 548/101, 106; 546/2, 6

[56] References Cited

U.S. PATENT DOCUMENTS

| | | | |
|---|---|---|---|
| 2,166,076 | 7/1939 | Rosenblatt | 556/137 |
| 4,140,707 | 2/1979 | Cleare et al. | 556/137 |
| 4,169,846 | 10/1979 | Kidani et al. | 556/137 |
| 4,203,912 | 5/1980 | Hydes et al. | 556/137 |
| 4,234,499 | 11/1980 | Hoeschele et al. | 556/137 |
| 4,242,430 | 12/1980 | Hara et al. | 556/137 X |
| 4,255,347 | 3/1981 | Kidani et al. | 556/137 |
| 4,256,652 | 3/1981 | Kidani et al. | 556/137 |
| 4,359,425 | 11/1982 | Totani et al. | 556/137 |
| 4,410,544 | 10/1983 | Berg et al. | 556/137 |
| 4,452,812 | 6/1984 | Macquet | 556/137 |
| 4,457,926 | 7/1984 | Amundsen et al. | 549/210 |
| 4,462,998 | 7/1984 | Amundsen et al. | 549/210 |

FOREIGN PATENT DOCUMENTS

| | | |
|---|---|---|
| 0055300 | 7/1982 | European Pat. Off. . |
| 2055377 | 3/1981 | United Kingdom . |
| 2128615 | 5/1984 | United Kingdom . |

OTHER PUBLICATIONS

Hall et al., J. Inorg. Biochem. 11 139–149 (1979).
Chemical Abstracts 93 125663v(1980).
Chemical Abstracts 88 570c (1978).
Chemical Abstracts 84 54030n (1976).
Speer et al., J. Clin. Hematol. Oncology 7(3) 856(1977).

Primary Examiner—Helen M. S. Sneed
Attorney, Agent, or Firm—Scully, Scott, Murphy & Presser

[57] ABSTRACT

Diaminocyclohexane platinum complexes having the structural formula

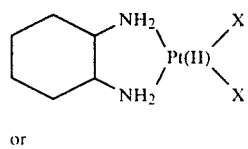

or

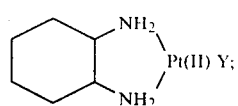

wherein:
X is a monovalent anion selected from the group consisting of isoascorbate, monosaccharate, saccharate-4-lactone, shikimate, isethionate, 2-aminoethylsulfate, azetidinecarboxylate, proline, hydroxyproline, pipecolinate, cyclopropanecarboxylate, cyclobutanecarboxylate, cyclopentanecarboxylate, cyclopentenecarboxylate, cyclohexanecarboxylate, cyclohexenecarboxylate, bicine, glycine, 2-aminoethanesulfonate, 2-chloroethanesulfonate and
Y is a divalent anion selected from the group consisting of iminodiacetate, isocitratelactone, furanedicarboxylate, cyclopropane-1,1-dicarboxylate, isocitratomonoethylester, N-methyliminodiacetate, N-(2-hydroxyethyl)-iminodiacetate, N-benzyliminodiacetate, N-phenyliminodiacetate, N-(2-acetamido)iminodiacetate, cyclohexane-1,1-diacetate, trans-1,2-cyclopropanedicarboxylate, trans-1,2-cyclobutanedicarboxylate, trans-1,2-cyclopentanedicarboxylate and trans-1,2-cyclohexanedicarboxylate and their use in the treatment of tumors.

86 Claims, No Drawings

DIAMINOCYCLOHEXANE PLATINUM COMPLEXES

CROSS-REFERENCE TO RELATED APPLICATIONS

This application is a continuation-in-part of U.S. application Ser. No. 636,522, filed Aug. 1, 1984, now abandoned, which, in turn, is a continuation-in-part of application Ser. No. 505,965, filed June 20, 1983, now abandoned.

BACKGROUND OF THE INVENTION

The present invention relates to certain novel 1,2-diaminocyclohexane platinum complexes and their use in the treatment of tumors.

Recently, certain platinum complexes have been shown by Rosenberg, et al. and others to be highly active anti-tumor agents (see U.S. Pat. Nos. 4,177,263 and 4,140,707). For example, the complex cis-dichlorodiamineplatinum-II or "cisplatin" is the chemotherapeutic agent of choice in the treatment of many and varied tumors.

There are several drawbacks, however, associated with the use of the platinum complexes to treat tumors. Generally, the platinum complexes have a relatively low solubility in water thereby rendering it difficult to formulate a composition which can effectively deliver the reagent to the site of the tumor in the body.

Moreover, many of the platinum complexes are highly nephrotoxic thereby further restricting their use in the absence of precautionary measures to avoid damage to the kidneys when administered to animals afflicted with tumors.

Recently, considerable activity has centered on the use of 1,2-diaminocyclohexane complexes of platinum as anti-tumor agents. See, for example, U.S. Pat. Nos. 3,892,790; 3,904,663; 4,115,418; 4,140,707; 4,169,846; 4,175,133; 4,228,090 and 4,256,652 and German Offenlegungschrift No. 30 22 917.

Although the complexes described therein possess anti-tumor activity, virtually all are highly insoluble in water and are also relatively highly nephrotoxic.

German Offenlegungschrift No. 30 22 957 describes 1,2-diaminocyclohexane/ascorbate complexes of platinum, useful as anti-tumor agents, which comprise mixtures of complexes having varying ratios of ascorbate ion to platinum. Thus, the publication discloses complexes of the formula:

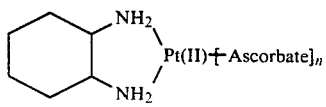

wherein n varies from 1.2 to 1.5. The complexes are described as poorly water soluble.

in the Proceedings for the American Association for Cancer Research, Vol. 23, page 116, 1982, we describe New Platinum Complexes Containing Ascorbate having good aqueous solubility, useful antitumor activity and decreased nephrotoxicity. Two such complexes, one containing Pt, aminoethylpyrrolidine and ascorbate and the second containing Pt, 1,2-diaminocyclohexane, chloride and ascorbate are capable of suppressing the growth of L1210 cells in vivo.

J. Am. Chem. Soc. 1985, 107, 274–276 describes the synthesis of a series of cis-[Pt(RNH$_2$)$_2$] (ascorbate) complexes which are reported to be stable in aqueous or alcoholic solutions and are active in the S180a tumor screen.

We have now found that certain other 1,2-diaminocyclohexane (DACH)-platinum-anion complexes are vastly superior to the ascorbate complexes in being relatively non-nephrotoxic, possessing a high degree of antitumor activity, high water-solubility, and no cross resistance to cis(DACH)-dichlorodiamine platinum II. In particular, we have found that the iminodiacetatocyclohexane platinum (II) complexes have marked in vitro cytotoxic activity, good in vivo activity as a single injection which is significantly enhanced when administered intraperitoneally and significantly less nephrotoxicity than cis-platin.

Especially preferred embodiments of this invention include the mixed isomer DACH-Pt (II) iminodiacetato complexes and the trans-R,R-DACH-Pt (II) mono-iminodiacetato, mono-N-methyl-iminodiacetato, mono-N-hydroxyethyliminodiacetato, mono-N-phenyliminodiacetato, and mono-N-benzyliminodiacetato complexes. These complexes are especially valuable in that they enhance the cytotoxicity without increased host toxicity.

It is an object of the present invention to provide non-nephrotoxic 1,2-diaminocyclohexane (DACH)-platinum-anion complexes containing 1.0 bidentate or 2 monodentate negatively charged organic radicals per molecule of platinum possessing high degrees of anti-tumor activity, high water-solubilities, and no cross resistance to cis-dichlorodiammine platinum II.

It is a further object of the invention to provide a method for the preparation of the platinum complexes.

It is a further object of the invention to provide a method for preparing DACH-platinum-anion complexes containing stoichiometric ratios of anion to platinum.

It is a further object of the invention to provide a pharmaceutical composition particularly adapted for the treatment of animals afflicted with tumors.

It is a further object of the invention to provide a therapeutic method for the treatment of animals afflicted with tumors.

SUMMARY OF THE INVENTION

The above and other objects of the invention are achieved by the hereinbelow described method which enables the production of complexes of DACH-platinum complexes of the following formulae which contain stoichiometric ratios of anion to platinum:

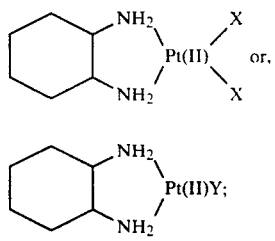

wherein:

X is a monovalent anion selected from the group consisting of isoascorbate, monosaccharate, saccharate-4-lactone, shikimate, isethionate, 2-aminoethylsulfate, azetidinecarboxylate, proline, hydroxyproline, pipecolinate, cyclopropanecarboxylate, cyclobutanecarboxylate, cyclopentanecarboxylate, cyclopentenecarboxylate, cyclohexanecarboxylate, cyclohexenecarboxylate, bicine, glycine, 2-aminoethanesulfonate, 2-chloroethanesulfonate, and Y is a divalent anion selected from the group consisting of iminodiacetate, isocitratelactone, furanedicarboxylate, cyclopropane-1,1-dicarboxylate and isocitratomonoethyl ester, N-methyliminodiacetate, N-(2-hydroxyethyl)-iminodiacetate, N-benzyliminodiacetate, N-phenyliminodiacetate, N-(2-acetamido)-iminodiacetate, cyclohexane-1,1-diacetate, trans-1,2-cyclobutanedicarboxylate, trans-1,2-cyclopentanedicarboxylate and trans-1,2-cyclohexanedicarboxylate The present invention is comprised of a central platinum metal coordinated to the DACH molecule and either two identical monodentates or one bidentate. Although cis and trans platinum complexes may be possible, the preferred geometric isomers are the squareplanar cis-platinum(II) complexes.

In addition, the DACH molecule contains two chiral centers, and, therefore, exists as either the cis-diastereomer or the trans-diastereomer. Although the cis-diastereomer is optically inactive, the transdiastereomer exists in two enantiometric forms: the trans-R,R-DACH and the trans-S,S-DACH. The trans-DACH are the preferred diastereomers. Especially preferred are the trans-R,R-DACH. It is to be noted that mixtures of the various isomers mentioned hereinabove are contemplated to be within the scope of the present invention.

Particularly useful complexes within the scope of the present invention are cis-bis-ascorbato (trans-R,R-DACH) platinum (II) and cis-bis-ascorbato (trans-S,S-DACH) platinum (II).

The most preferred embodiments of the present invention are the iminodiacetato derivatives of the trans-DACH-platinum complexdes. Of these, particularly preferred iminodiacetato derivatives are the trans-R,R-DACH-Pt(II) complexes of the above formula wherein:

Y is mono-iminodiacetate, mono-N-methyliminodiacetate, mono-N-hydroxyethyliminodiacetate, mono-N-phenyliminodiacetate, and mono-N-benzyliminodiacetate.

The method of the invention for preparing the above-described complexes comprises:

(a) reacting a water-soluble haloplatinate (II) in an aqueous medium with DACH to produce a di-halo-(DACH)-platinum (II);

(b) reacting said product of step (a) with a soluble sulfate salt in an aqueous medium to produce sulfato(-DACH)-platinum(II);

(c) reacting the product of step (b) with a soluble salt of X or Y to produce said complex of the above formula, and (d) recovering said complex.

The present invention also provides a pharmaceutical composition in unit dosage form suitable for administration to an animal afflicted with tumor cells sensitive to a platinum complex of the above formula comprising a therapeutically anti-tumor effective amount of the platinum complex and a pharmaceutically acceptable carrier therefor.

The invention also provides a method for the treatment of an animal afflicted with tumor cells sensitive to a platinum complex of the above formula comprising administering to the animal a therapeutically, anti-tumor effective amount of the platinum complex.

DETAILED DESCRIPTION OF THE INVENTION

The complexes of the invention have the following structural formulae:

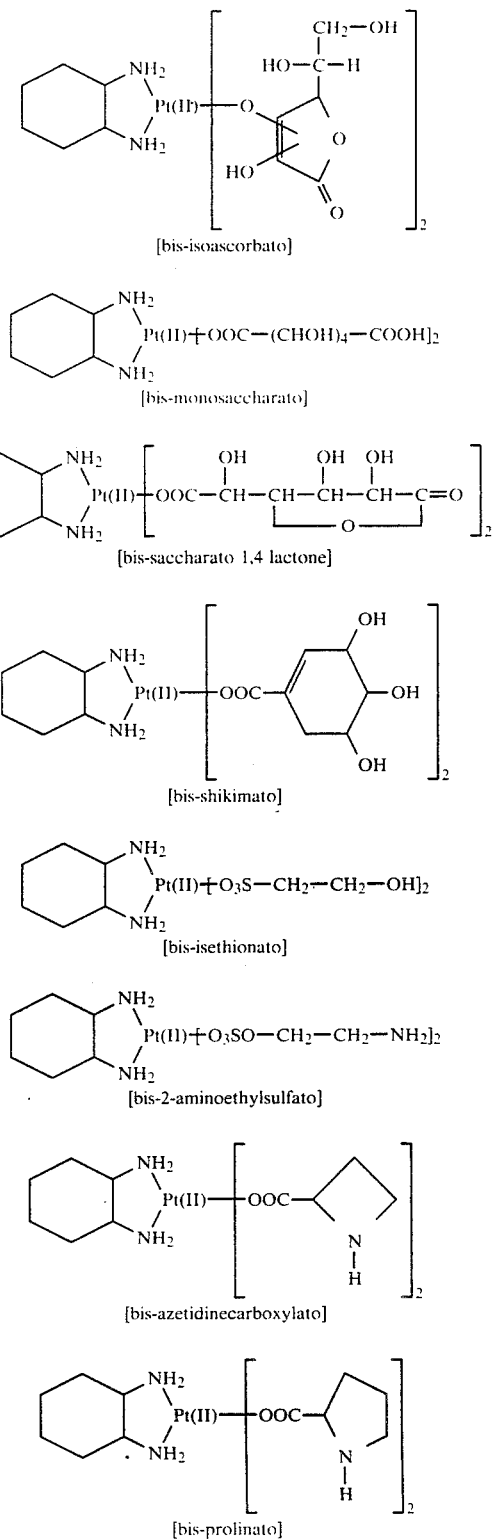

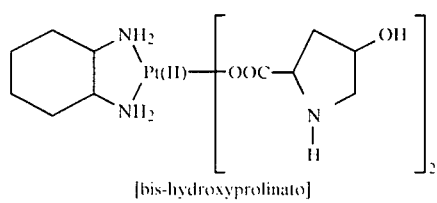
[bis-hydroxyprolinato]

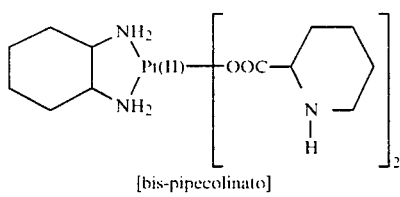
[bis-pipecolinato]

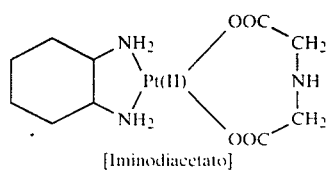
[Iminodiacetato]

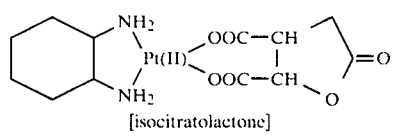
[isocitratolactone]

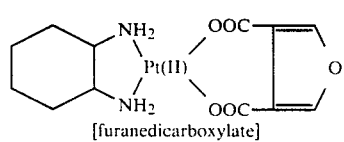
[furanedicarboxylate]

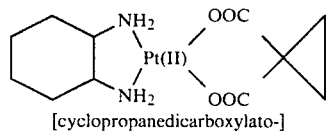
[cyclopropanedicarboxylato-]

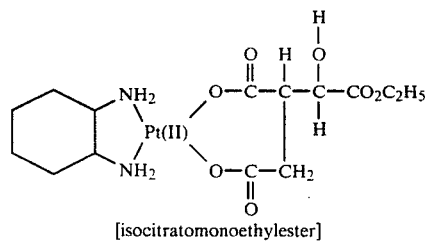
[isocitratomonoethylester]

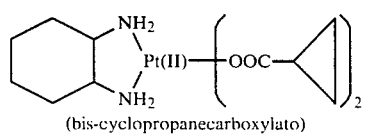
(bis-cyclopropanecarboxylato)

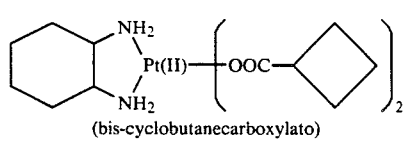
(bis-cyclobutanecarboxylato)

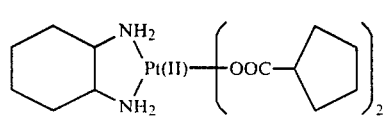

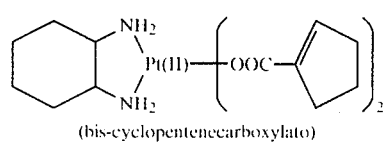
(bis-cyclopentanecarboxylato)

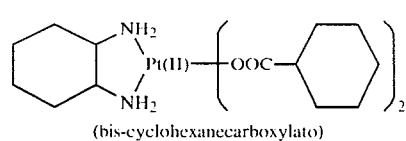
(bis-cyclopentenecarboxylato)

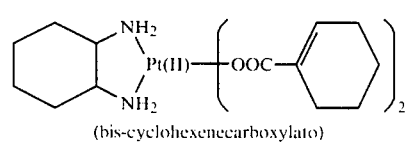
(bis-cyclohexanecarboxylato)

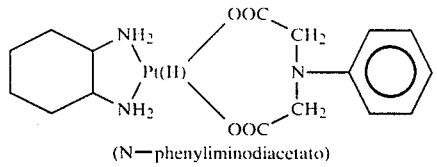
(bis-cyclohexenecarboxylato)

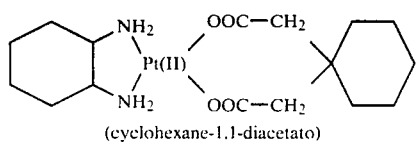
(N—phenyliminodiacetato)

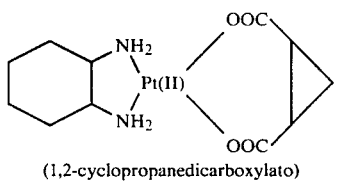
(cyclohexane-1,1-diacetato)

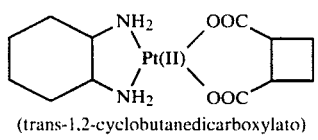
(1,2-cyclopropanedicarboxylato)

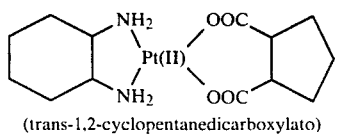
(trans-1,2-cyclobutanedicarboxylato)

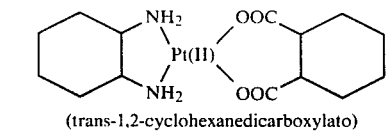
(trans-1,2-cyclopentanedicarboxylato)

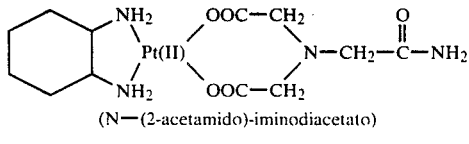
(trans-1,2-cyclohexanedicarboxylato)

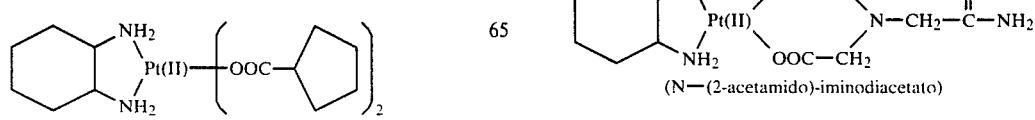
(N—(2-acetamido)-iminodiacetato)

-continued

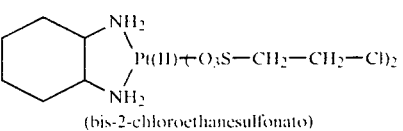
(bis-2-chloroethanesulfonato)

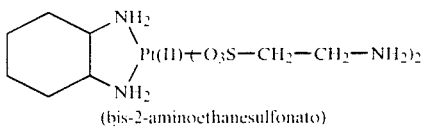
(bis-2-aminoethanesulfonato)

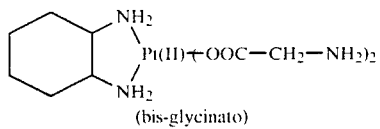
(bis-glycinato)

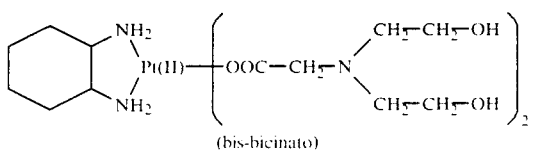
(bis-bicinato)

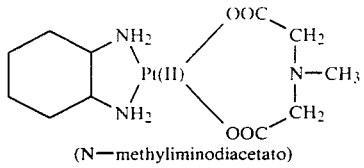
(N—methyliminodiacetato)

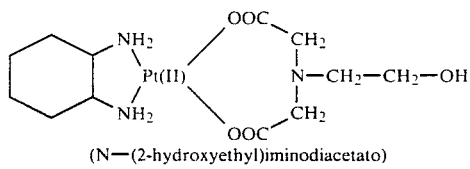
(N—(2-hydroxyethyl)iminodiacetato)

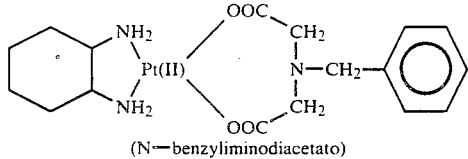
(N—benzyliminodiacetato)

The stoichiometric mono- and bis-anion-(DACH) platinum complexes of the invention (i.e., containing one divalent anion or two monovalent anions per molecule of platinum) may be prepared by reacting any suitable watersoluble haloplatinate (i.e., $K_2PtCl_4$) with DACH to produce the intermediate, di-halo-(DACH)-platinum(II). The reaction is preferably effected in water at room temperature for a time sufficient to drive the reaction to completion, generally from about 6 to 8 hours.

The intermediate di-halo complex is normally a yellow solid precipitate which is advantageously isolated from the reaction mixture by filtering, followed by washing with water, methanol and acetone. Finally, the yellow solid is dried, preferably under vacuum or is left in solution and immediately reacted therein with a sulfate. It is preferred to utilize a sulfate of a metal or cation the halo salt of which is insoluble in water to facilitate isolation of the product. Thus, where the di-halo (DACH) platinum is the di-chloro complex, it is preferred to employ $Ag_2SO_4$ thereby facilitating removal of the insoluble by-product, AgCl. The reaction is preferably carried out in an aqueous medium such as water or in the reaction medium from the first step of the method at room temperature. The reaction generally goes to completion in from about 18 to about 24 hours.

Following removal of the insoluble by-product halide, the intermediate sulfato (DACH-platinum(II)) is isolated by evaporating the yellow filtrate to dryness, e.g., using a rotary evaporator, as a yellow-brown solid which is washed, e.g., with acetone and dried, preferably, in vacuum. Alternatively, the sulfato-DACH-platinum intermediate is left in solution and reacted therein with a soluble salt of the appropriate anion to yield the platinum complex of the invention.

It is preferred to utilize a metal or other cation salt of the anion whose by-product sulfate salt is insoluble in water to facilitate isolation of the platinum complex. For example, the use of the barium salt of the anion yields barium sulfate as a by-product which is readily removable from the reaction medium by filtration.

The reaction is preferably conducted in an aqueous medium at about room temperature for a time sufficient to drive the reaction to completion, generally from about 0.3 to about 0.5 hours.

The platinum complex may be isolated from the reaction medium by filtering the by-product barium sulfate. The yellow filtrate is evaporated to dryness at 45°–50° C. under reduced pressure, e.g., using a rotary evaporator. The yellow brown solid is then dried, e.g., over $P_2O_5$ under vacuum.

A reaction sequence for preparing the bis ascorbate complex, for example, is depicted by the following equations wherein:

L = DACH, and

Asc = ascorbate $K_2PtCl_4 + L \rightarrow LPtCl_2 + 2KCl$ $LPtCl_2 + Ag_2SO_4 \rightarrow LPtSO_4 + 2AgCl$ $LPtSO_4 + Ba(Asc)_2 \rightarrow LPt(Asc)_2 + BaSO_4$ It is to be understood that is is within the scope of the method of the present invention to employ similar synthetic procedures to prepare suitable aryl, aralkyl or alkyl N-substituted iminodiacetato DACH platinum complexes.

It is likewise apparent that by using similar synthetic procedures mixed isomer DACH,trans-R,R-DACH, trans-S,S-DACH or cis-DACH may be readily prepared and used as the stable amine ligand for the platinum coordination complexes of the present invention.

The method of the invention is illustrated by the following non-limiting examples. The products of preparative examples 1–13, 22, 23 and 24 are summarized in Table I.

TABLE 1

| COMPOUND NO. | COMPOUND | EXAMPLE NO. |
|---|---|---|
| 1 | cis-bis-dichloro(DACH)Pt(II) | 1 |
| 2 | sulfato(DACH)Pt(II) | 2 |

TABLE 1-continued

| COMPOUND NO. | COMPOUND | EXAMPLE NO. |
|---|---|---|
| 3 | cis-bis-ascorbato(DACH)Pt(II).1H$_2$O | 3 |
| 4 | cis-bis-ascorbato(trans-R,R—DACH)Pt(II).3H$_2$O | 4 |
| 5 | cis-bis-ascorbato(trans-S,S—DACH)Pt(II).2H$_2$O | 5 |
| 6 | cis-bis-ascorbato(cis-DACH)Pt(II).5H$_2$O | 6 |
| 7 | cis-bis-isoascorbato(DACH)Pt(II).3H$_2$O | 7 |
| 8 | cis-bis-D-monosaccharato(DACH)Pt(II).3H$_2$O | 8 |
| 9 | cis-bis-D-saccharato-1,4-lactone(DACH)Pt(II) | |
| 10 | cis-bis-shikimato(DACH)Pt(II).2H$_2$O | 10 |
| 11 | iminodiacetato(DACH)Pt(II).2H$_2$O | 11 |
| 12 | DL-isocitratolactone(DACH)Pt(II).1H$_2$O | 12 |
| 13 | cis-bis-isethionato(DACH)Pt(II).2H$_2$O | 13 |
| 14 | cis-bis-2-aminoethylsulfato(DACH)Pt(II) | 13 |
| 15 | cis-bis-L-azetidinecarboxylato(DACH)Pt(II).1H$_2$O | 13 |
| 16 | cis-bis-L-prolinato(DACH)Pt(II) | 13 |
| 17 | cis-bis-L-hyroxyprolinato(DACH)Pt(II).1H$_2$O | 13 |
| 18 | cis-bis-DL-pipecolinato(DACH)Pt(II).1H$_2$O | 13 |
| 19 | furanedicarboxylato(DACH)Pt(II) | 13 |
| 20 | cyclopropane-1,1-dicarboxylato(DACH)Pt(II).H$_2$O | 13 |
| 21 | isocitratomonoethylester(DACH)Pt(II).1.5H$_2$O | 13 |
| 22 | Cis-bis-cyclohexanecarboxylato(DACH)Pt(II).1H$_2$O | 24 |
| 23 | 1,1-cyclohexanediacetato(DACH)Pt(II).1H$_2$O | 24 |
| 24 | Cis-bis-cyclohexenecarboxylato(DACH)Pt(II).1H$_2$O | 24 |
| 25 | Cis-bis-cyclopentanecarboxylato(DACH)Pt(II).1H$_2$O | 24 |
| 26 | Cis-bis-cyclopentenecarboxylato(DACH)Pt(II).2H$_2$O | 24 |
| 27 | trans-DL-1,2-cyclopentanedicarboxylato(DACH)Pt(II) | 24 |
| 28 | N—Methyliminodiacetato(DACH)Pt(II).1H$_2$O | 24 |
| 29 | Cis-bis-cyclopropanecarboxylato(DACH)Pt(II).1H$_2$O | 24 |
| 30 | Cis-bis-cyclobutanecarboxylato(DACH)Pt.1H$_2$O | 24 |
| 31 | Cis-bis-ethanesulfonato(DACH)Pt(II).H$_2$O | 24 |
| 32 | Cis-bis-glycinato(DACH)Pt(II).1H$_2$O | 24 |
| 33 | Cis-bis-chloroethanesulfonato(DACH)Pt(II).1H$_2$O | 24 |
| 34 | Cis-bis-bicinato(DACH)Pt(II) | 24 |
| 35 | Iminodiacetato(trans-R,R—DACH)Pt(II).2H$_2$O | 23 |
| 36 | Cis-bis-L-prolinato(trans-R,R—DACH)Pt(II).2H$_2$O | 22 |
| 37 | N—Phenyliminodiacetato(DACH)Pt(II).2H$_2$O | 24 |
| 38 | N—Benzyliminodiacetato(DACH)Pt(II) | 24 |
| 39 | N—(2-Hydroxyethyl)-iminodiacetato(DACH)Pt(II).2H$_2$O | 24 |
| 40 | trans-1,2-cyclopropanedicarboxylato(DACH)Pt(II) | 24 |
| 41 | trans-1,2-cyclobutanedicarboxylato(DACH)Pt(II) | 24 |
| 42 | N—(2-Acetamido)-iminodiacetato(DACH)Pt(II).½H$_2$O | 24 |
| 43 | trans-1,2-cyclohexanedicarboxylato(DACH)Pt(II) | 24 |

EXAMPLE 1

Cis-bis-dichloro(DACH)platinum(II)

To an aqueous filtered solution of K$_2$PtCl$_4$(3.5 g; 8.4 mmole in 50 ml of water) 0.9416 g (8.4 mmole) of DACH was added. The reaction mixture was stirred at room temperature for 6-8 hours. A yellow solid was precipitated, filtered, washed with water, methanol and finally with acetone. The final product was dried under vacuum.

Yield=56%.

Cis-bis-dichloro(trans-1-DACH)platinum(II); cis-bis-dichloro(trans-d-DACH)platinum(II) and cis-bis-dichloro(cis-DACH)platinum(II) were prepared in an analogous manner using stoichiometric amounts (ca. 1 mmole) of K$_2$PtCl$_4$ and the respective DACH isomers, i.e., trans-l, trans-d and cis-.

EXAMPLE 2

Sulfato(DACH)platinum(II)

Dichloro(DACH)platinum(II) (DACH being a mixture-, trans-l-, trans-d- or cis-isomer) (1.0 g; 2.6 mmole) was suspended in water (20 ml), and a solution of Ag$_2$SO$_4$ (0.75 g; 2.4 mmole) in water (150 ml) was added. The reaction mixture was stirred at room temperature for 24 hours in the dark. The precipitated AgCl was filtered off, and the yellow filtrate was evaporated to dryness at 45°-50° C. under reduced pressure using a rotary evaporator. A yellow-brown produce was obtained and dried over P$_2$O$_5$ under vacuum.

Yield: 90%.

EXAMPLE 3

Cis-bis-ascorbate(DACH)platinum(II).1H$_2$O

Sulfato(DACH)platinum(II).H$_2$O 0.846 g (2 mmole) was dissolved in water (50 ml) and barium ascorbate (0.974 g; 2 mmole in 30 ml of water) was added thereto. The reaction mixture was stirred ca. 20 minutes at room temperature. Barium sulfate precipitate was filtered off, and the yellow filtrate was evaporated to dryness at 45°–50° C. under reduced pressure using a rotary evaporator. A brown yellow product was obtained, which was then washed with acetone. The product was finally dried under vacuum.

Yield = 90%. The analytical data for the product is set forth in Table II.

Platinum analysis-calculated for C$_{18}$H$_{28}$N$_2$O$_{12}$Pt.1-H$_2$O: Pt28.80%, Found: 28.72%.

EXAMPLE 4

Cis-bis-ascorbato(trans-R,R-DACH)platinum(II).3H$_2$O

Sulfato(trans-R,R-DACH)platinum(II) 0.423 g (1 mmole) was dissolved in water (20 ml) and a solution of barium ascorbate (0.478 g; 1 mmole in 10 ml of water) was added thereto. The reaction mixture was stirred for 20 minutes. Barium sulfate precipitate was filtered off, and the yellow filtrate was evaporated to dryness at 45°–50° C. under reduced pressure using a rotary evaporator. A brown yellow solid was obtained, which was then washed with acetone and dried in vacuo.

Yield = 85%. The analytical data for the product is set forth in Table II.

EXAMPLE 5

Cis-bis-ascorbato(trans-S,S-DACH)platinum(II).2H$_2$O

Sulfato(trans-SS-DACH)platinum(II) 0.423 g (1 mmole) was dissolved in water (20 ml) and a solution of barium ascorbate (0.487; 1 mmole) in 10 ml of water) was added thereto. The reaction mixture was stirred at room temperature for 20 minutes. Barium sulfate precipitate was filtered off, and the brown yellow filtrate was evaporated to dryness at 45°–50° C. under reduced pressure using a rotary evaporator. A yellow solid was obtained which was then washed with acetone and dried under vacuum.

Yield = 85%. The analytical data for the product is set forth in Table II.

EXAMPLE 6

Cis-bis-ascorbato(cis-DACH)platinum(II)

Sulfato(cis-DACH)platinum(II) 0.211 g (0.5 mmole) was dissolved in water (10 ml) and a solution of barium ascorbate (0.244 g; 0.5 mmole in 10 ml of water) was added thereto. The reaction mixture was stirred at room temperature for 20 minutes. Barium sulfate precipitate was filtered off, and the yellow filtrate was evaporated to dryness at 45°–50° C. under reduced pressure using a rotary evaporator. A brown yellow solid was obtained, which was then washed with acetone and dried in vacuo.

Yield = 80%. The analytical data for the product is set forth in Table II.

EXAMPLE 7

Cis-bis-isoascorbato(DACH)platinum(II).3H$_2$O

Sulfato(DACH)platinum(II) 0.423 g (1 mmole) was dissolved in water (20 ml) and a solution of barium isoascorbate (0.487 g; 1 mmole in 10 ml of water) was added thereto. The reaction mixture was stirred at room temperature for 20 minutes. Barium sulfate precipitate was filtered off, and the yellow filtrate was evaporated to dryness at 45°–50° C. under reduced pressure using a rotary evaporator. A brown yellow product was obtained, which was then washed with acetone. The product was finally dried in vacuo.

Yield = 85%. The analytical data for the product is set forth in Table II.

Platinum analysis-calculated for C$_{18}$H$_{28}$N$_2$O$_{12}$Pt.3-H$_2$O: Pt 27.34%. Found: Pt 27.56%.

EXAMPLE 8

Cis-bis-D-monosaccharato(DACH)platinum(II).3H$_2$O

Sulfato(DACH)platinum(II) 1.04 g (2.47 mmole) was dissolved in water (50 ml) and a solution of barium monosaccharate (1.372 g; 2.47 mmole in 80 ml of water) was added thereto. The reaction mixture was stirred at room temperature for 20 minutes. Barium sulfate precipitate was filtered off, and the yellow filtrate was evaporated to dryness at 45°–50° C. under reduced pressure using a rotary evaporator. A brown yellow solid was obtained, which was then washed with acetone and dried in vacuo.

Yield = 89%. The analytical data for the product is set forth in Table II.

Platinum Analysis-calculated for C$_{18}$H$_{32}$N$_2$O$_{16}$Pt.3-H$_2$O: Pt 24.96%. Found: Pt 24.77%.

EXAMPLE 9

Cis-bis-D-saccharate-1,4-lactone(DACH)platinum(II)

Sulfato(DACH)platinum(II) 0.106 g was dissolved in 10 ml of water and barium saccharate-1,4-lactone, prepared in situ by the addition of Ba(OH)$_2$.8H$_2$O 0.075 g to an aqueous solution of D-saccharic acid 1,4 lactone monohydrate 0.11 g was added thereto and the reaction mixture was stirred for 30 minutes at room temperature. Barium sulfate precipitate was filtered off and the yellow filtrate was evaporated to dryness at 45°–50° C. under reduced pressure using a rotary evaporator. A brown yellow solid was obtained, which was then washed with methanol and acetone. The product was finally dried in vacuo.

Yield = 82%. The analytical data for the product is set forth in Table II.

EXAMPLE 10

Cis-bis-shikimato(DACH)platinum(II)

Sulfato(DACH)platinum(II) 0.423 g (1 mmole) was dissolved in water (20 ml) and a solution of barium shikimate (0.483 g; 1 mmole in 50 ml of water) was added thereto. The reaction mixture was stirred at room temperature for 20 minutes. Barium sulfate precipitate was filtered off, and the yellow filtrate was evaporated to dryness at 45°–50° C. under reduced pressure using a rotary evaporator. A brown yellow solid was obtained, which was then washed with acetone and dried in vacuo.

Yield = 80%. The analytical data for the product is set forth in Table II.

Platinum Analysis-Calculated for C$_{20}$H$_{32}$N$_2$O$_{10}$Pt.2-H$_2$O Pt 28.20%. Found: Pt 28.76%.

EXAMPLE 11

Iminodiacetato(DACH)platinum(II)

Sulfato(DACH)platinum(II) 1.04 g (2.47 mmole) was dissolved in water (50 ml) and a solution of barium iminodiacetate (0.663 g; 2.57 mmole in 50 ml of water) was added thereto. The reaction mixture was stirred at room temperature for 20 minutes. Barium sulfate precipitate was filtered off, and the yellow filtrate was evaporated to dryness at 45°–50° C. under reduced pressure using a rotary evaporator. A brown yellow solid was obtained, which was then washed with acetone and dried in vacuo.

Yield = 79%. The analytical data for the product is set forth in Table II.

EXAMPLE 12

DL-Isocitratolactone(DACH)platinum(II)

Sulfato(DACH)platinum(II) 0.106 g (0.25 mmole) was dissolved in water (10 ml) and a solution of barium isocitratolactone (0.766 g; 0.25 mmole in 20 ml of water) was added thereto. The reaction mixture was stirred at room temperature for 20 minutes. Barium sulfate precipitate was filtered off, and the yellow filtrate was evaporated to dryness at 45°–50° C. under reduced pressure using a rotary evaporator. A brown yellow solid was obtained, which was then washed with acetone and dried in vacuo.

Yield = 75%. The analytical data for the product is set forth in Table II.

The other complexes of the invention, i.e., bis-isethionato, bis-2-aminoethylsulfato, bis-azetidinecarboxylato, bis-prolinato, bis-hydroxyprolinato, bis-pipecolinato, and isocitratomonoethyl ester were prepared in an analogous manner to the methods of Example 9, using stoichiometric amounts (ca. 1 mmole) sulfato(DACH)-platinum(II) and the respective barium salts, i.e., isethionate, 2-aminoethylsulfate, azetidinecarboxylate, proline, hydroxyproline, pipecolinate, and isocitratemonoethyl ester.

It will be understood by those skilled in the art that the various isomeric DACH (i.e., trans-S,S-, trans-R,R-, cis-) can be prepared according to the methods of the above examples employing the appropriate DACH isomer. The analytical data for the compounds prepared in Examples 1–13 are set forth in Table II.

TABLE II

| COMPOUND NO. | ANALYTICAL DATA | | | | | |
|---|---|---|---|---|---|---|
| | FOUND (%) | | | CALCULATED (%) | | |
| | C | H | N | C | H | N |
| 3 | 32.15 | 4.32 | 3.85 | 31.90 | 4.43 | 4.13 |
| 4 | 30.01 | 4.53 | 3.70 | 30.28 | 4.76 | 3.92 |
| 5 | 31.28 | 4.38 | 3.93 | 31.07 | 4.60 | 4.03 |
| 6 | 28.94 | 4.01 | 3.73 | 28.83 | 5.07 | 3.74 |
| 7 | 30.25 | 4.19 | 3.93 | 30.28 | 4.76 | 3.92 |
| 8 | 27.16 | 4.23 | 3.23 | 27.64 | 4.86 | 3.58 |
| 9 | 29.66 | 4.15 | 3.53 | 29.70 | 3.85 | 3.85 |
| 10 | 34.60 | 5.11 | 3.75 | 34.72 | 5.20 | 4.05 |
| 11 | 25.35 | 4.83 | 8.57 | 25.20 | 4.83 | 8.82 |
| 12 | 28.65 | 4.13 | 5.42 | 28.85 | 4.00 | 5.61 |
| 13 | 19.62 | 4.16 | 4.19 | 20.16 | 4.70 | 4.70 |
| 14 | 20.28 | 4.62 | 8.99 | 20.36 | 4.41 | 9.50 |
| 15 | 31.98 | 5.20 | 10.48 | 31.86 | 5.31 | 10.62 |
| 16 | 35.63 | 5.77 | 9.87 | 35.73 | 5.58 | 10.42 |
| 17 | 32.75 | 5.57 | 9.39 | 32.69 | 5.11 | 9.53 |
| 18 | 37.30 | 6.21 | 9.46 | 37.03 | 6.17 | 9.70 |
| 19 | 28.84 | 3.53 | 5.33 | 28.80 | 4.00 | 5.60 |
| 20 | 29.37 | 4.44 | 5.50 | 28.94 | 4.60 | 6.14 |
| 21 | 30.10 | 4.46 | 5.32 | 30.32 | 4.87 | 5.05 |

TABLE II-continued

The in vitro anti-tumor activities of the complexes of the invention are illustrated by the following examples:

EXAMPLE 14

Wild type L1210 leukemic cells were grown as a suspension culture in McCoy's 5A medium supplemented with 10% horse serum, glutamine, streptomycin and penicillin at 37° C., 95% relative humidity and 5% $CO_2$. Four ml of cell suspension ($10^5$ cells/ml) are added to culture tubes and the appropriate concentration (0.01, 0.1, 1 or 10 μg/ml final concentration) of drug added to the culture tubes. After 72 hours of incubation, the cell concentration of control and experimental cultures are determined with the aid of a Coulter Counter ® Model ZB$_f$ and the percent inhibition calculated.

| COMPOUND NUMBER | $ID_{50}$(μg/ml) |
|---|---|
| 3 | 5.0 |
| 4 | 1.9 |
| 5 | 4.4 |
| 6 | 4.0 |
| 7 | 4.1 |
| 8 | 2.8 |
| 9 | 3.0 |
| 10 | 2.5 |
| 11 | 4.2 |
| 12 | 1.0 |
| 13 | 0.43 |
| 14 | 4.3 |
| 15 | 3.6 |
| 16 | 4.0 |
| 17 | 2.7 |
| 18 | 0.44 |
| 19 | 1.0 |
| 20 | 0.41 |
| 21 | 2.0 |

The lack of cross-resistance of complexes of the invention to cisdiamminedichloroplatinum(II) is illustrated below:

EXAMPLE 15

L1210 leukemia cells (L1210/PDD) which are more than 50 fold resistant to cisdiamminedichloroplatinum(II) were grown as suspension cultures in McCoy's 5A supplemented with 10% horse serum, glutamine, penicillin and streptomycin at 37° C., 95% relative humidity and 5% $CO_2$. Four ml of cell suspension were added to culture tubes and the appropriate concentration (0.01, 0.1, 1 or 10 μg/ml final drug concentration) was added. After 96 hours the cell concentration of control and experimental cultures were calculated with the aid of a Coulter Counter ® Model ZB$_f$ and the percent inhibition calculated.

| COMPOUND NUMBER | $ID_{50}$(μg/ml) | |
|---|---|---|
| | L1210/0 | L1210/PDD |
| 3 | 5.0 | 2.6 |
| 4 | 1.9 | 0.4 |
| 5 | 4.4 | 2.3 |
| 8 | 2.8 | 0.9 |
| 9 | 3.0 | 0.6 |

-continued

| COMPOUND NUMBER | ID$_{50}$(μg/ml) | |
|---|---|---|
| | L1210/0 | L1210/PDD |
| 10 | 2.5 | 1.2 |
| 11 | 4.2 | 1.6 |
| cisdiamminedichloro-platinum(II) | 0.1 | 5.5 |

The anti-tumor activities of the complexes of the invention are illustrated by the following example:

EXAMPLE 16

BDF$_1$ mice were inoculated intraperitoneally with 10$^6$ L1210 cells. About 24 hours after inoculation of the cells, the mice were injected intraperitoneally with varying dosages of complexes of the present invention. Six mice were used for each dosage level in each experiment with an equal number of control mice inoculated with 10$^6$ L1210 cells and left untreated with a given complex. The results [%T/C=(survival time of treated animals/survival time of control animals)×100] are set forth below. Long term survival signifies that animals were alive 60 days after inoculation with L1210 cells.

| COMPOUND NUMBER | DOSE(mg/kg) | % T/C | Long Term Survivors |
|---|---|---|---|
| 3 | 50 | 125 | — |
| | 60 | 163 | — |
| | 75 | 143 | — |
| | 90 | 145 | — |
| | 100 | Toxic | — |
| 4 | 25 | 128 | — |
| | 50 | 184 | 1/6 |
| 5 | 25 | 136 | — |
| | 50 | Toxic | — |
| 6 | 50 | Toxic | — |
| | 100 | Toxic | — |
| 7 | 25 | 132 | — |
| | 50 | 136 | — |
| | 100 | 196* | 1/6 |
| *2/6 animals died of apparent drug toxicity | | | |
| 8 | 12.5 | 120 | — |
| | 25 | 129 | — |
| | 50 | 156 | — |
| | 100 | 151 | — |
| | 200 | Toxic | — |
| 9 | 12.5 | 127 | — |
| | 25 | 138 | — |
| | 50 | 156 | — |
| | 100 | Toxic | — |
| 10 | 50 | 140 | — |
| | 100 | 217 | 2/6 |
| 11 | 50 | 163 | — |
| | 100 | 109* | — |
| 12 | 25 | 133 | — |
| | 50 | 145 | — |
| | 100 | Toxic | — |
| *Apparent Toxicity | | | |
| 13 | 5 | 153 | — |
| | 10 | 180 | — |
| | 20 | 140* | 1/6 |
| | 50 | Toxic | — |
| *2/6 animals died of apparent drug toxicity | | | |
| 14 | 6.25 | | |
| | 12.5 | In | |
| | 25 | Progress | |
| | 50 | | |
| 15 | 12.5 | 157 | — |
| | 25 | 148 | — |
| | 50 | 161 | — |
| | 100 | Toxic | — |
| 16 | 12.5 | 144 | — |
| | 25 | 165 | — |
| | 50 | 165 | — |
| | 100 | 162* | — |
| *1 animal died from apparent toxicity | | | |
| 17 | 25 | 160 | — |
| | 50 | 170 | — |
| | 100 | Toxic | — |
| 18 | 12.5 | 145 | — |
| | 25 | 180 | — |
| | 50 | Toxic | — |
| 19 | 6.25 | 143 | — |
| | 12.5 | 136 | — |
| | 25 | 136 | — |
| | 50 | Toxic | — |

EXAMPLE 17

The procedure of Example 16 was repeated except that the treated animals were injected with multiple doses of the complex as indicated below:

| COMPOUND NUMBER | DOSE (mg/kg) | Day of Administration | % T/C | Long Term Survivors |
|---|---|---|---|---|
| 3 | 25 | 1,5,9 | 176 | — |
| | 10 | 1,5,9 | 123 | — |
| | 20 | 1,5,9 | 196 | 1/6 |
| | 30 | 1,5,9 | 257 | 1/6 |
| | 30 | 1,5,9,13 | 273 | 1/6 |
| | 2.5 | 1-9 | 113 | — |
| | 5 | 1-9 | 142 | — |
| | 10 | 1-9 | 184 | — |
| | 20 | 1-9 | 239 | 1/6 |
| 4 | 25 | 1,5,9 | 218 | — |
| | 50 | 1,5,9 | 144 | — |
| 7 | 12.5 | 1,5,9 | 151 | — |
| | 25 | 1,5,9 | 179 | — |
| | 50 | 1,5,9 | 212 | — |
| 8 | 25 | 1,5,9 | 206 | — |
| | 50 | 1,5,9 | 225 | 1/6 |
| 10 | 12.5 | 1,5,9 | 139 | — |
| | 25 | 1,5,9 | 149 | — |
| | 50 | 1,5,9 | 222 | 1/6 |
| 11 | 25 | 1,5,9 | 199 | — |
| | 50 | 1,5,9 | 220 | 2/6 |
| 12 | 25 | 1,5,9 | 219 | — |
| | 50 | 1,5,9 | 165 | — |

EXAMPLE 18

The anti-tumor activity of compound number 3 was evaluated against cells sensitive to (L1210/0) and resistant to (L1210/PDD) the standard platinum complex cis-diamminedichloroplatinum(II).

| DOSE(mg/kg) | SCHEDULE | % T/C | SURVIVORS |
|---|---|---|---|
| L1219/PDD | | | |
| 6.25 | 1,5,9 | 115 | — |
| 12.5 | 1,5,9 | 124 | — |
| 25 | 1,5,9 | 135 | — |
| 50 | 1,5,9 | 223 | 3/10 |
| 100 | 1,5,9 | 172* | — |
| L1210/0 | | | |
| 6.25 | 1,5,9 | 117 | — |
| 12.5 | 1,5,9 | 135 | — |
| 25 | 1,5,9 | 181 | 2/10 |
| 50 | 1,5,9 | 247 | 1/10 |
| 100 | 1,5,9 | 104 | — |

*Toxicity apparent as excessive loss of weight

The acute toxicity data obtained with selected complexes of the invention are set forth below:

EXAMPLE 19

Male albino mice were administered a single intraperitoneal injection of the appropriate test compound and were observed daily for signs of toxicity and survival. Fourteen days after treatment all surviving mice were sacrificed and the $LD_{10}$, $LD_{50}$ and $LD_{90}$ were calculated.

| COMPOUND NUMBER | DOSE (mg/kg) | DEATHS/ TREATED |
|---|---|---|
| 3 | 110 | 1/6 |
|   | 125 | 2/6 |
|   | 140 | 4/6 |
|   | 155 | 6/6 |
|   | 175 | 6/6 |
| Calculated $LD_{10}$ 108 mg/kg | | |
| Calculated $LD_{50}$ 125 mg/kg | | |
| Calculated $LD_{90}$ 150 mg/kg | | |
| 5 | 60 | 0/6 |
|   | 80 | 2/6 |
|   | 100 | 5/6 |
|   | 125 | 6/6 |
|   | 160 | 5/6 |
| Calculated $LD_{10}$ 70 mg/kg | | |
| Calculated $LD_{50}$ 90 mg/kg | | |
| Calculated $LD_{90}$ 125 mg/kg | | |
| 8 | 100 | 1/6 |
|   | 125 | 1/6 |
|   | 158 | 4/6 |
|   | 200 | 3/6 |
|   | 250 | 6/6 |
| Calculated $LD_{10}$ 115 mg/kg | | |
| Calculated $LD_{50}$ 155 mg/kg | | |
| Calculated $LD_{90}$ 220 mg/kg | | |
| 9 | 85 | 0/6 |
|   | 100 | 0/6 |
|   | 125 | 3/6 |
|   | 158 | 5/6 |
|   | 200 | 4/6 |
| Calculated $LD_{10}$ 100 mg/kg | | |
| Calculated $LD_{50}$ 140 mg/kg | | |
| Calculated $LD_{90}$ 185 mg/kg | | |
| 10 | 50 | 0/6 |
|   | 100 | 1/6 |
|   | 125 | 3/6 |
|   | 160 | 5/6 |
|   | 200 | 3/6 |
| Calculated $LD_{10}$ 85 mg/kg | | |
| Calculated $LD_{50}$ 130 mg/kg | | |
| Calculated $LD_{90}$ 205 mg/kg | | |
| 11 | 85 | 1/6 |
|   | 100 | 3/6 |
|   | 125 | 5/6 |
|   | 158 | 4/6 |
|   | 200 | 6/6 |
| Calculated $LD_{10}$ 80 mg/kg | | |
| Calculated $LD_{50}$ 115 mg/kg | | |
| Calculated $LD_{90}$ 155 mg/kg | | |

The potential nephrotoxicity of selected complexes of the invention are set forth below:

EXAMPLE 20

Male albino mice were administered a single intraperitoneal injection of either the calculated $LD_{10}$ or $LD_{50}$ of the test compound. Blood was then obtained by retroorbital puncture 96 hours after treatment for determination of blood urea nitroben (BUN) levels (a standard method of screening compounds for potential renal toxicity).

| COMPOUND NUMBER | RELATIVE DOSE | BUN (mg/100 ml) |
|---|---|---|
| 3 | $LD_{10}$ | 25 ± 6 |
|   | $LD_{50}$ | 23 ± 6 |
| 5 | $LD_{10}$ | 31 ± 3 |
|   | $LD_{50}$ | 38 ± 9 |
| 8 | $LD_{10}$ | 31 ± 8 |
|   | $LD_{50}$ | 35 ± 12 |
| 9 | $LD_{10}$ | 38 ± 8 |
|   | $LD_{50}$ | 50 ± 15 |
| 10 | $LD_{10}$ | 40 ± 7 |
|   | $LD_{50}$ | 39 ± 5 |
| 11 | $LD_{10}$ | 36 ± 12 |
|   | $LD_{50}$ | 38 ± 10 |
| 0.09% NaCl | — | 32 ± 2 |
| cis diamminedichloro platinum(II) | $LD_{10}$ | 53 ± 19 |
|   | $LD_{50}$ | 67 ± 10 |

EXAMPLE 21

Cis-bis-2-aminoethanesulfonato(DACH)platinum(II)

Sulfato(DACH)platinum(II), 0.211 g, was dissolved in 10 of water and barium-2-amino-ethanesulfonate, prepared in situ by the addition of $Ba(OH)_2.8H_2O$, 0.15 g, to an aqueous solution of 2-aminoethanesulfonic acid, 0.125 g, was added thereto and the reaction mixture was stirred for 30 minutes at room temperature. Barium sulfate precipitate was filtered off and the yellow filtrate was evaporated to dryness at 45°–50° C. under reduced pressure using a rotary evaporator. A brown yellow solid was obtained which was then washed with methanol and acetone. The product was obtained which was then washed with methanol and acetone. The product was finally dried in vacuo.

Yield = 80%.

The analytical data for the product are set forth in Table III.

EXAMPLE 22

Cis-bis-L-prolinato(trans-R,R-DACH)platinum(II)

Sulfato (trans-R,R-DACH)platinum(II) (0.11 g) was dissolved in 20 ml of water and the barium salt of L-proline, prepared in situ by the addition of $Ba(OH)_2.8H_2O$ (0.150 g) to an aqueous solution of L-proline (0.115 g) was added thereto and the reaction mixture was stirred for 20–30 minutes at room temperature. Barium sulfate precipitate was filtered off and the yellow filtrate was evaporated to dryness at 45°–50° C. under reduced pressure using a rotary evaporator. A yellowish-white solid was obtained which was then washed with methanol and acetone. The product was finally dried in vacuo:

Yield = 75%.

The analytical data for the product are set forth in Table III.

EXAMPLE 23

Iminodiacetato(trans-R,R-DACH)platinum(II)2H$_2$O

Sulfato(trans-R,R-DACH)platinum(II), 0.423 g, was dissolved in 50 ml of water and barium iminodiacetate prepared in situ by the addition of $Ba(OH)_2.8H_2O$, 0.3 g, to an aqueous solution of iminodiacetic acid, 0.133 g in 100 ml water was added thereto and the reaction mixture was stirred for 20–30 minutes at room temperature. Barium sulfate precipitate was filtered off and the yellow filtrate was evaporated to dryness at 45°–50° C. under reduced pressure using a rotary evaporator. A yellowish-white solid was obtained which was then washed with acetone. The product was then dried in vacuo. Yield=70%.

The analytical data for the product are set forth in Table III.

EXAMPLE 24

Cis-bis-cyclopropanecarboxylato(DACH)platinum(II)

Sulfato(DACH)platinum(II), 0.423 g (1 mmole), was dissolved in water (20 ml) and barium cyclopropanecarboxylate, prepared in situ by the addition of $Ba(OH)_2 \cdot 8H_2O$ (0.30 g) to an aqueous solution of cyclopropanecarboxylic acid (0.172 g) (2 mmole), was added thereto and the reaction mixture was stirred for 20–30 minutes at room temperature. Barium sulfate precipitate was filtered off and the yellow filtrate was evaporated to dryness at 45°–50° C. under reduced pressure using a rotary evaporator. A brown yellow solid was obtained, which was purified from methanol. The product was finally dried in vacuo. Yield=70%. The analytical data for the products are set forth in Table III.

Other complexes of the invention, i.e. bis-cyclobutanecarboxylate, bis-cyclopentanecarboxylato, bis-cyclopentenecarboxylato, bis-cyclohexanecarboxylato, bis-cyclohexenecarboxylato, cyclopropane-1,1-dicarboxylato, trans-DL-1,2-cyclopentanecarboxylato, cyclohexane-1,1-diacetato, bicinato, chloroethanesulfonato, N-(2-hydroxyethyl)-iminodiacetato, N-(2-acetamido)-iminodiacetato, N-methyliminodiacetato, N-phenyl-iminodiacetato, N-benzyl-iminodiacetato, 3,4-furanedicarboxylato, trans-1,2-cyclopropane dicarboxylato, trans-1,2-cyclobutanedicarboxylato, trans-1,2-cyclopentané dicarboxylato and trans-1,2-cyclohexanedicarboxylato were prepared in an analogous manner to the above mentioned method using stoichiometric amounts (ca/1 mmole) sulfato (DACH) platinum (II), and the respective barium salts (prepared in situ) i.e. cyclobutanecarboxylate, cyclopentanecarboxylate, cyclopentenecarboxylate, cyclohexanecarboxylate, cyclohexenecarboxylate, cyclopropane-1,1-dicarboxylate, trans-DL-1, 2-cyclopentanedicarboxylate, cyclohexane-1,1-diacetate, bicinate, chloroethanesulfonate, N-(2-hydroxy-ethyl)iminodiacetate, N-(2-acetamido)iminodiacetate, N-methyliminoacetate, N-phenyliminoacetate, N-benzyliminodacetate, 3,4-furanedicarboxylate, trans-1,2-cyclopropanedicarboxylate, trans-1,2-cyclobutanedicarboxylate, trans-1,2-cyclopentanedicarboxylate and trans-1, 2-cyclohexanedicarboxylate.

TABLE III

| COMPOUND NO. | Analytical Data Found (%) | | | Calculated (%) | | |
|---|---|---|---|---|---|---|
| | C | H | N | C | H | N |
| 22 | 41.23 | 6.93 | 5.46 | 41.30 | 6.54 | 4.82 |
| 23 | 36.58 | 5.75 | 5.03 | 36.55 | 5.71 | 5.33 |
| 24 | 41.20 | 5.47 | 4.64 | 41.56 | 5.89 | 4.85 |
| 25 | 38.82 | 5.29 | 5.04 | 39.06 | 6.14 | 5.06 |
| 26 | 37.77 | 5.52 | 4.97 | 37.95 | 5.62 | 4.92 |
| 27 | 33.43 | 4.58 | 5.45 | 33.50 | 4.72 | 6.01 |
| 28 | 27.95 | 5.16 | 8.58 | 27.96 | 4.87 | 8.89 |
| 29 | 33.40 | 5.31 | 5.48 | 33.79 | 5.23 | 5.63 |
| 30 | 36.61 | 5.72 | 5.21 | 36.55 | 5.71 | 5.33 |
| 31 | 20.77 | 5.05 | 9.51 | 20.86 | 4.86 | 9.73 |
| 32 | 25.31 | 5.32 | 11.64 | 25.25 | 5.05 | 11.78 |
| 33 | 18.26 | 3.91 | 3.78 | 18.46 | 3.69 | 4.30 |
| 34 | 33.98 | 5.43 | 8.33 | 34.00 | 5.98 | 8.81 |
| 35 | 25.14 | 4.37 | 8.59 | 25.20 | 4.83 | 8.82 |
| 36 | 33.41 | 5.76 | 9.47 | 33.50 | 5.93 | 9.77 |
| 37 | 34.65 | 4.94 | 7.99 | 34.77 | 4.89 | 7.60 |
| 38 | 38.50 | 5.20 | 7.31 | 38.47 | 4.71 | 7.92 |
| 39 | 27.96 | 5.15 | 7.62 | 27.69 | 5.19 | 8.07 |
| 40 | 27.96 | 4.43 | 5.57 | 27.90 | 4.65 | 5.92 |

TABLE III-continued

| COMPOUND NO. | Analytical Data Found (%) | | | Calculated (%) | | |
|---|---|---|---|---|---|---|
| | C | H | N | C | H | N |
| 41 | 31.64 | 4.83 | 5.85 | 31.93 | 4.43 | 6.21 |
| 42 | 28.34 | 5.22 | 10.47 | 28.45 | 4.54 | 11.00 |
| 43 | 33.86 | 5.62 | 5.40 | 33.12 | 5.12 | 5.52 |

In Vitro Cytotoxicity

The following compounds were tested for in vitro cytotoxicity according to the protocol described in Example 14.

| Compound No. | $ID_{50}$ (μg/ml) |
|---|---|
| 22 | 0.5 |
| 23 | 0.6 |
| 24 | 1.0 |
| 25 | 0.3 |
| 26 | 1.3 |
| 27 | 0.4 |
| 28 | 1.6 |
| 29 | 0.3 |
| 30 | 0.4 |
| 31 | 3.1 |
| 32 | 2.5 |
| 33 | 0.3 |
| 34 | 1.2 |
| 35 | 3.0 |
| 36 | 0.8 |
| 37 | 1.0 |
| 38 | 2.3 |
| 39 | 3.0 |
| 40 | 0.4 |
| 41 | 0.5 |
| 42 | 0.7 |

In Vivo Efficacy Studies—Single Dose

The following compounds were tested for in vivo oncolytic activity following a single i.p. injection of the drug according to the protocol described in Example 16.

| Compound No. | Dose (mg/kg) | % T/C | LTS |
|---|---|---|---|
| 25 | 50 | 163 | — |
| | 25 | 178 | — |
| | 12.5 | 161 | — |
| 27 | 50 | 183 | — |
| | 25 | 159 | — |
| | 12.5 | 158 | — |
| 28 | 50 | Toxic | — |
| | 25 | 185 | — |
| | 12.5 | 161 | — |
| 29 | 50 | 199 | 1/6 |
| | 25 | 176 | — |
| | 12.5 | 252 | 1/6 |
| 30 | 50 | 145 | — |
| | 25 | 154 | — |
| | 12.5 | 149 | — |
| 26 | 50 | 157 | — |
| | 25 | 158 | — |
| | 12.5 | 185 | — |
| 31 | 50 | 153 | — |
| | 25 | 134 | — |
| | 12.5 | 109 | — |
| 32 | 50 | 158 | — |
| | 25 | 131 | — |
| | 12.5 | 128 | — |
| 33 | 50 | Toxic | — |
| | 25 | 144 | — |
| | 12.5 | 188 | — |
| 34 | 50 | 160 | — |
| | 25 | 151 | — |

-continued

| Compound No. | Dose (mg/kg) | % T/C | LTS |
|---|---|---|---|
| | 12.5 | 165 | — |
| 36 | 50 | 149 | — |
| | 25 | 212 | 1/6 |
| | 12.5 | 179 | — |
| 37 | 50 | 108 | — |
| | 25 | 156 | — |
| | 12.5 | 172 | — |
| 38 | 50 | 158 | — |
| | 25 | 170 | — |
| | 12.5 | 123 | — |
| 22 | 100 | 170 | — |
| | 50 | 140 | — |
| 24 | 100 | 105 | — |
| | 50 | 165 | — |
| | 25 | 132 | — |

In Vivo Efficacy Studies—Multiple Dose

The following complexes were tested in vivo oncolytic activity following 3 i.p. injections (days 1, 5, 9) according to the protocol described in Examples 16 and 17.

| Compound No. | Dose (mg/kg) | % T/C | LTS |
|---|---|---|---|
| 25 | 25 | 253 | — |
| | 12.5 | 246 | — |
| | 6.25 | 202 | — |
| 26 | 25 | 300 | 1/6 |
| | 12.5 | 356 | 1/6 |
| | 6.25 | 189 | — |
| 31 | 100 | 295 | 2/6 |
| | 50 | 198 | 1/6 |
| 37 | 25 | 242 | 1/6 |
| | 12.5 | 298 | 5/6 |
| | 6.25 | 246 | 3/6 |
| 38 | 25 | 240 | 2/6 |
| | 12.5 | 287 | 1/6 |
| | 6.25 | 277 | — |

T/C calculated for 30 day observation period. Long term survivor data represents survivors/treated 50 days after treatment.

EXAMPLE 25

Mixed isomer DACH-Pt-(II)-L-complexes listed in Table IV below were prepared in an analogous manner to the methods of Example 8, using the stoichiometric amounts (ca. 1 mmole) sulfato-(DACH)-platinum (II) and the appropriate barium salt.

TABLE IV

| Mixed isomer DACH-Pt-(II)-L-Complexes | |
|---|---|
| Complex (L =) | Identifier No. |
| bis-ascorbato | 1 |
| bis-isoascorbato | 2 |
| bis-monosaccharato | 3 |
| bis-shikimato | 4 |
| bis-prolinato | 5 |
| bis-aminoethylsulfato | 6 |
| bis-saccharato-1,4-lactone | 7 |
| mono-furanedicarboxylato | 8 |
| mono-isocitratomonoethylester | 9 |
| mono-iminodiacetato | 10 |
| mono-N—methyliminodiacetato | 11 |
| mono-N—hydroxyethyliminodiacetato | 12 |
| mono-N—(2-acetamido)iminodiacetato | 13 |
| mono-N—phenyliminodiacetato | 14 |
| mono-N—benzyliminodiacetato | 15 |

EXAMPLE 26

Trans-R,R-DACH-Pt(II) complexes listed in Table V below were prepared in a manner analogous to the method of Example 25 using sulfato-(trans-R,R-DACH)-platinum(II) and the appropriate barium salt.

TABLE V

| Trans-R,R-DACH-Pt(II)-L-Complexes | |
|---|---|
| Complex (L =) | Identifier No. |
| Mono-iminodiacetato | 10a |
| mono-N—methyliminodiacetato | 11a |
| mono-N—hydroxyethyliminodiacetato | 12a |
| mono-N—phenyliminodiacetato | 14a |
| mono-N—benzyliminodiacetato | 15a |

The analytical data for the products of Examples 25 and 26 are set forth in Table VI below:

TABLE VI

| | ANALYTICAL DATA | | | | | |
|---|---|---|---|---|---|---|
| | Observed (%) | | | Calculated (%) | | |
| Identifier No. | C | H | N | C | H | N |
| 1 | 32.15 | 4.32 | 3.85 | 31.90 | 4.43 | 4.13 |
| 2 | 30.25 | 4.19 | 3.93 | 30.28 | 4.16 | 3.92 |
| 3 | 27.16 | 4.23 | 3.23 | 27.64 | 4.56 | 3.58 |
| 4 | 34.60 | 5.11 | 3.75 | 34.72 | 5.20 | 4.05 |
| 5 | 35.63 | 5.77 | 9.87 | 35.73 | 5.58 | 10.12 |
| 6 | 20.28 | 4.62 | 8.99 | 20.36 | 4.41 | 9.30 |
| 7 | 29.66 | 4.15 | 3.53 | 29.70 | 3.85 | 3.85 |
| 8 | 28.84 | 3.53 | 5.33 | 28.80 | 4.00 | 5.60 |
| 9 | 30.10 | 4.46 | 5.32 | 30.32 | 4.87 | 5.05 |
| 10 | 25.35 | 4.83 | 8.57 | 25.20 | 4.83 | 8.82 |
| 10a | 25.27 | 4.79 | 8.63 | 25.20 | 4.83 | 8.82 |
| 11 | 27.95 | 5.16 | 8.58 | 27.96 | 4.87 | 8.89 |
| 11a | 28.00 | 5.05 | 8.67 | 27.96 | 4.87 | 8.89 |
| 12 | 27.96 | 5.15 | 7.62 | 27.69 | 5.19 | 8.07 |
| 12a | 27.75 | 5.22 | 8.00 | 27.69 | 5.19 | 8.07 |
| 13 | 28.34 | 5.22 | 10.74 | 28.45 | 5.54 | 11.00 |
| 13a | 28.39 | 5.32 | 10.85 | 28.45 | 5.54 | 11.00 |
| 14 | 34.65 | 4.94 | 7.99 | 34.77 | 4.89 | 7.60 |
| 14a | 34.69 | 4.88 | 7.84 | 34.77 | 4.89 | 7.60 |
| 15 | 38.50 | 5.20 | 7.31 | 38.47 | 4.71 | 7.82 |
| 15a | 38.45 | 5.16 | 7.43 | 38.47 | 4.71 | 7.82 |

In Vitro Cytotoxicity

The complexes listed in Example 25 and 26 were tested for in vitro cytotoxicity according to the protocol described in Example 14. The results are shown in Tables VII and VIII below.

TABLE VII

| Cytoxicity Data of DACH Pt-L Complexes | | | |
|---|---|---|---|
| | $ID_{50}$ (μg/ml) | | Resistance |
| Complex (L=) | L1210/0 | L1210/DDP | Factor |
| bis-ascorbato | 5.0 | 5.0 | 1.0 |
| bis-isoascorbato | 4.1 | 3.8 | 0.9 |
| bis-monosaccharato | 2.8 | 0.9 | 0.3 |
| bis-shikimato | 2.5 | 1.2 | 0.5 |
| bis-prolinato | 4.0 | 2.5 | 0.6 |
| bis-aminoethylsulfato | 4.3 | 3.7 | 0.9 |
| bis-saccharato-1,4-lactone | 3.0 | 0.6 | 0.2 |
| mono-furanedicarboxylato | 1.0 | 0.9 | 0.9 |
| mono-isocitratomono-ethylester | 2.0 | 1.9 | 0.9 |
| mono-iminodiacetato | 4.2 | 1.6 | 0.4 |
| mono-N—methyliminodiacetato | 1.6 | 1.3 | 0.8 |
| mono-N—hydroxyethyliminodiacetato | 0.7 | 0.9 | 1.3 |
| mono-N—(2-acetamido)iminodiacetato | 3.0 | 1.8 | 0.6 |
| mono-N—phenyliminodiacetato | 2.3 | 2.6 | 1.1 |

TABLE VII-continued

Cytoxicity Data of DACH Pt-L Complexes

| Complex (L = ) | ID$_{50}$ (μg/ml) L1210/0 | L1210/DDP | Resistance Factor |
|---|---|---|---|
| mono-N—benzylimino-diacetato | 1.0 | 0.8 | 0.8 |
| DDP | 0.1 | 5.5 | 55 |

TABLE VIII

Cytotoxicity Data for the trans-R,R-DACH Pt-L Complexes

| Complex (L = ) | ID$_{50}$(μg/ml) L1210/0 | L1210/DDP | Resistance Factor |
|---|---|---|---|
| mono-iminodiacetato | | | |
| mono-N—methylimino-diacetato | 0.8 | 1.9 | 2.4 |
| mono-N—hydroxyethyl-iminodiacetato | 1.4 | 1.8 | 1.3 |
| mono-N—phenylimino-diacetato | 0.7 | 0.6 | 0.8 |
| mono-N—benzylimino-diacetato | 1.0 | 2.4 | 2.4 |
| DDP | 0.1 | 5.5 | 55 |

In Vivo Efficacy vs. L1210/0

BDF$_1$ mice were innoculated intraperitoreally with $10^6$ L1210 leukemia cells and treatment was begun on the next day (day 1). Two treatment schedules, i.e. single i.p. injection of the drug and i.p. injections on days 1, 5 and 9 according to the protocol described in Examples 16 and 17 were used.

The data appears below in Table IX and X.

TABLE IX

In Vivo Efficacy of DACH Iminodiacetato Complexes Administered as Single i.p. Injection

| Complex (L = ) | Maximal Effective Dose (mg/Kg) | % T/C |
|---|---|---|
| H$_3$ | 50 | 163 |
| CH$_3$ | 25 | 180 |
| C$_2$H$_5$OH | 25 | 180 |
| C$_6$H$_5$ | 12.5 | 172 |
| CH$_2$—C$_6$H$_5$ | 25 | 170 |
| DDP | 9 | 150 |

$(a)$ % T/C = $\frac{\text{mean survival time (treated)}}{\text{mean survival time (control)}} \cdot 100$ $(b)$ DDP = diamminedichloroplatinum II

TABLE X

In Vivo Efficacy of DACH-Pt-Iminodiacetato Complexes Administered i.p. on Days 1, 5 and 9

| Complex (L=) | Maximal Effective Dose (mg/kg) | % T/C | Long Term$^a$ Survivors |
|---|---|---|---|
| H$_3$ | 50 | 220 | 2/6 |
| CH$_3$ | 12.5 | 550 | 5/6 |
| C$_2$H$_5$OH | 25 | 450 | 4/6 |
| C$_6$H$_5$ | 12.5 | 537 | 4/6 |
| CH$_2$—C$_6$H$_5$ | 12.5 | 397 | 2/6 |
| DDP | 5 | 210 | 1/6 |

$^a$Long Term Survivors = animals alive 60 days after tumor inoculation with no visible signs of tumor at sacrifice.

Table XI below shows the in vivo efficacy results obtained with trans-R,R-DACH Pt-iminodiacetato complexes.

TABLE XI

In Vivo Efficacy of trans-R,R-DACH Pt-Iminodiacetato Complexes Administered i.p. on Days 1, 5 and 9

| Complex (L = ) | Maximal Effective Dose (mg/kg) | % T/C | Long Term Survivors |
|---|---|---|---|
| H | 25 | 437 | 2/6 |
| CH$_3$ | 6.25 | 700 | 6/6 |
| C$_2$H$_5$OH | 6.25 | 384 | 2/6 |
| C$_6$H$_5$ | 6.25 | 578 | 4/6 |
| CH$_2$—C$_6$H$_5$ | 6.25 | 620 | 4/6 |
| DDP | 5 | 220 | 1/6 |

The data show that the trans-R,R-DACH complexes are more potent than the mixed isomer DACH complexes and are much more effective than the DDP.

MELANOTIC MELANOMA TEST

The animals used were BDF$_1$ mice, all of the same sex, weighing a minimum of 18 g. and all within a 4 g. weight range. There were 6 animals per test group. The mice were inoculated intraperitoneally with $10^6$ viable B16 cells (day 0). The test compounds were administered intraperitoneally on days 1, 5 and 9 at various doses. The animals were weighed and survivors were recorded on a regular basis for 60 days. The median survival time and the ratio of survival time for treated (T)/control (C) animals were calculated. The positive control compound was DDP given intraperitoneally at 5 mg/kg. The criterion for efficacy is T/C×100≧125%. The results of the tests appear in Table XII below.

TABLE XII

Efficacy of DACH-Pt-Iminodiacetato Complexes Against i.p. Inoculated B16 Melanoma

| Complex (L = ) | Maximal Effective Dose (mg/kg) | % T/C | Long Term Survivors |
|---|---|---|---|
| CH$_3$(t) | 25 | 210 | 2/6 |
| CH$_3$(m) | 25 | 205 | 0/6 |
| C$_2$H$_5$OH(m) | 25 | 196 | 2/6 |
| C$_2$H$_5$OH(t) | 25 | 265 | 4/6 |
| C$_6$H$_5$(t) | 25 | 160 | 3/6 |
| C$_6$H$_5$(m) | 25 | 215 | 0/6 |
| CH$_2$—C$_6$H$_5$(t) | 12.5 | 252 | 3/6 |
| CH$_2$—C$_6$H$_5$(m) | 12.5 | 207 | 1/6 |
| DDP | 5 | 172 | 1/6 |

(m) = mixed isomer DACH
(t) = trans-R,R-DACH

These data show that at least three of the complexes tested were more effective than DDP against B16 and that all of the remaining complexes were at least as effective as DDP against B16.

TOXOCOLOGICAL STUDIES

The LD$_{10}$ and LD$_{50}$ values for a single intraperitoneal injection of the test compounds are shown in Table XIII below.

TABLE XIII

Acute Lethality Data for Mixed Isomer DACH Pt. Iminodiacetato Complexes

| | LD$_{10}$ | LD$_{50}$ (mg/kg) | LD$_{90}$ | RUN (mg/100 ml) (mean + 1 S.D.) |
|---|---|---|---|---|
| H | 53 | 107 | 169 | 23 ± 4 |
| CH$_3$ | 49 | 92 | 170 | 22 ± 3 |
| C$_2$H$_5$OH | 63 | 150 | 301 | 18 ± 2 |
| C$_6$H$_5$ | 56 | 81 | 135 | 18 ± 1 |
| CH$_2$—C$_6$H$_5$ | 81 | 140 | 210 | 27 ± 3 |
| DDP | 13 | 15.5 | 18 | 80 ± 8 |
| Control | | | | 25 ± 2 |

The platinum complexes of the invention may be compounded with suitable pharmaceutically acceptable carriers and administered orally, intramuscularly, topically, etc. It is preferred, however, to combine the complex with suitable media, e.g., 5% dextrose, klucel, water, etc., for intravenous administration. Care should be taken, however, to avoid the use of saline as an i.v. medium.

Those skilled in the art will be aware of suitable carriers for the complexes of the invention suitable for formulation into capsules, tablets, powders, ointments, pellets, inc.

The complexes may also be administered in combination with other anti-tumor agents in a combined chemotherapeutic regimen.

The amount of complex included in the pharmaceutical composition and the dosages of complex utilized in the method of treatment of the invention will vary depending in each case upon the condition of the patient, the nature of the tumor undergoing treatment, the anti-tumor activity of the complex, the toxicity and solubility characteristics thereof, etc. Generally, however, an amount of platinum complex ranging from about 25 to about 200 mg/kg is adequate for most applications.

We claim:

1. A water-soluble square-planar DACH cis-platinum(II) four-coordinate complex having the formula:

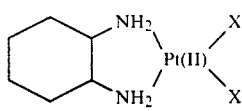

or

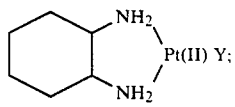

wherein:

X is a monovalent anion selected from the group consisting of, monosaccharate, saccharate-4-lactone, shikimate, isethionate, 2-aminoethylsulfate, azetidinecarboxylate, proline, hydroxyproline, pipecolinate, cyclopropanecarboxylate, cyclobutanecarboxylate, cyclopentanecarboxylate, cyclopentenecarboxylate, cyclohexanecarboxylate, cyclohexenecarboxylate, bicine, glycine, 2-aminoethanesulfonate, 2-chloroethanesulfonate and Y is a divalent anion selected from the group consisting of iminodiacetate, isocitratelactone, furanedicarboxylate, cyclopropane-1,1-dicarboxylate, isocitratomonoethylester, N-methyliminodiacetate, N-(2-hydroxyethyl)-iminodiacetate, N-benzyliminodiacetate, N-phenyliminodiacetate, N-(2-acetamido)iminodiacetate, cyclohexane-1,1-diacetate, trans-1,2-cyclopropanedicarboxylate, trans-1,2-cyclobutanedicarboxylate, trans-1,2-cyclopentanedicarboxylate and trans-1,2-cyclohexanedicarboxylate.

2. A platinum complex of claim 1 having the formula:

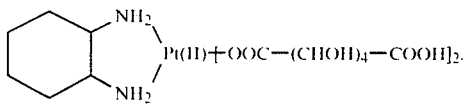

[bis-monosaccharato]

3. A platinum complex of claim 1 having the formula:

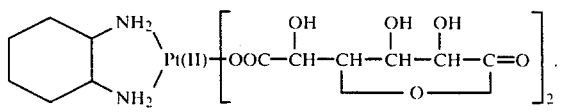

[bis-saccharato 1,4 lactone]

4. A platinum complex of claim 1 having the formula:

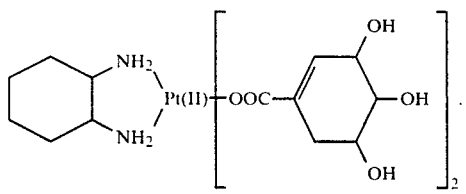

[bis-shikimato]

5. A platinum complex of claim 1 having the formula:

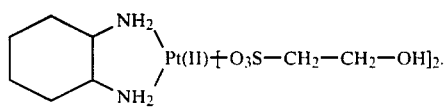

[bis-isethionato]

6. A platinum complex of claim 1 having the formula:

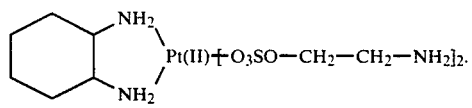

[bis-2-aminoethylsulfato]

7. A platinum complex of claim 1 having the formula:

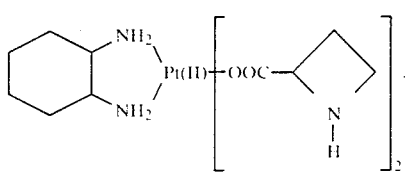

[bis-azetidinecarboxylato]

8. A platinum complex of claim 1 having the formula:

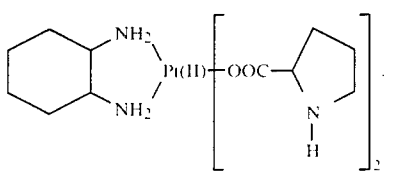

[bis-prolinato]

9. A platinum complex of claim 1 having the formula:

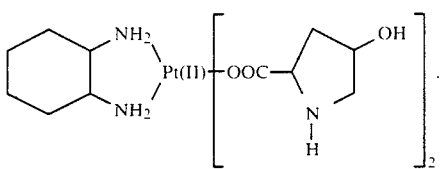

[bis-hydroxyprolinato]

10. A platinum complex of claim 1 having the formula:

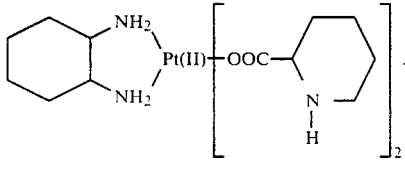

[bis-pipecolinato]

11. A platinum complex of claim 1 having the formula:

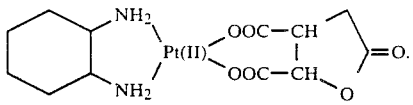

[isocitratolactone]

12. A platinum complex of claim 1 having the formula:

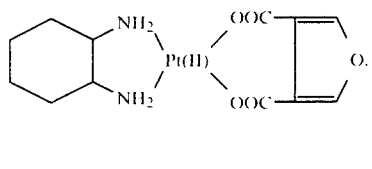

[furanedicarboxylate]

13. A platinum complex of claim 1 having the formula:

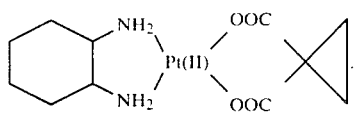

[cyclopropanedicarboxylato-]

14. A platinum complex of claim 1 having the formula:

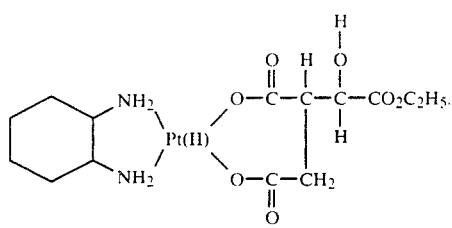

[isocitratomonoethylester]

15. A platinum complex of claim 1 having the formula:

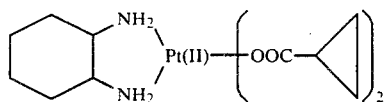

(bis-cyclopropanecarboxylato)

16. A platinum complex of claim 1 having the formula:

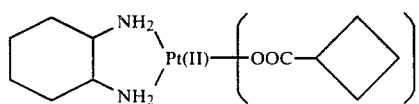

(bis-cyclobutanecarboxylato)

17. A platinum complex of claim 1 having the formula:

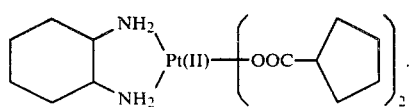

(bis-cyclopentanecarboxylato)

18. A platinum complex of claim 1 having the formula:

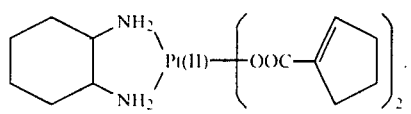

(bis-cyclopentenecarboxylato)

19. A platinum complex of claim 1 having the formula:

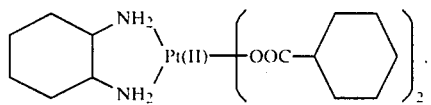

(bis-cyclohexanecarboxylato)

20. A platinum complex of claim 1 having the formula:

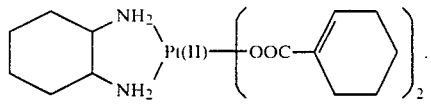

(bis-cyclohexenecarboxylato)

21. A platinum complex of claim 1 having the formula:

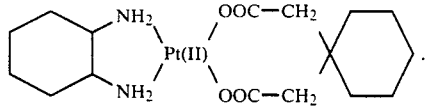

(cyclohexane-1,1-diacetato)

22. A platinum complex of claim 1 having the formula:

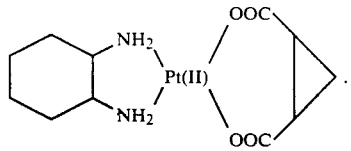

(1,2-cyclopropanedicarboxylato)

23. A platinum complex of claim 1 having the formula:

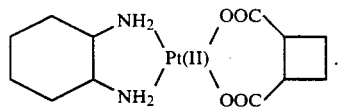

(trans-1,2-cyclobutanedicarboxylato)

24. A platinum complex of claim 1 having the formula:

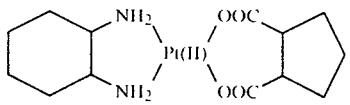

(trans-1,2-cyclopentanedicarboxylato)

25. A platinum complex of claim 1 having the formula:

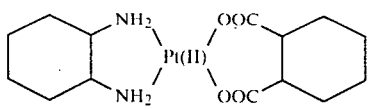

(trans-1,2-cyclohexanedicarboxylato)

26. A platinum complex of claim 1 having the formula:

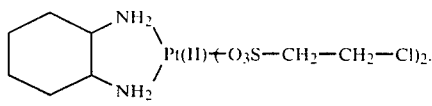

(bis-2-chloroethanesulfonato)

27. A platinum complex of claim 1 having the formula:

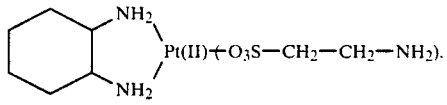

(bis-2-aminoethanesulfonato)

28. A platinum complex of claim 1 having the formula:

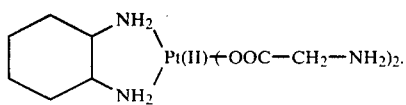

(bis-glycinato)

29. A platinum complex of claim 1 having the formula:

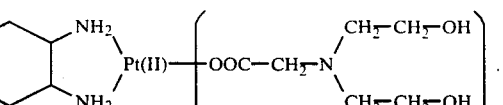

(bis-bicinato)

30. A water-soluble square-planar DACH cis-platinum (II) four-coordinate complex having the formula:

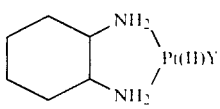

wherein Y is iminodiacetate, N-methyliminodiacetate, N-(2-hydroxyethyl)-iminodiacetate, N-phenyliminodiacetate or N-benzyliminodiacetate.

31. A complex according to claim 38 which is trans-R,R-DACH-Pt(II).

32. A platinum complex according to claim 1 wherein the complex is iminodiacetato(DACH)Pt(II).

33. A platinum complex according to claim 1 wherein the complex is iminodiacetato(trans-R,R-DACH)Pt(II).

34. A platinum complex according to claim 1 wherein the complex is N-methyliminodiacetato(DACH)Pt(II).

35. A platinum complex according to claim 1 wherein the complex is N-methyliminodiacetato(trans-R,R-DACH)Pt(II).

36. A platinum complex according to claim 1 wherein the complex is N-(2-hydroxyethyl)iminodiacetato(-DACH)Pt(II).

37. A platinum complex according to claim 1 wherein the complex is N-(2-hydroxyethyl)iminodiacetato(-trans-R,R-DACH)Pt(II).

38. A platinum complex according to claim 1 wherein the complex is N-phenyliminodiacetato(DACH)Pt(II).

39. A platinum complex according to claim 1 wherein the complex is N-phenyliminodiacetato(trans-R,R-DACH)Pt(II).

40. A platinum complex according to claim 1 wherein the complex is N-benzyliminodiacetato(DACH)Pt(II).

41. A platinum complex according to claim 1 wherein the complex is N-benzyliminodiacetato(trans-R,R-(DACH)Pt(II).

42. A platinum complex according to claim 1 wherein the complex is N-(2-acetamido)-iminodiacetato(-DACH)Pt(II).

43. A platinum complex according to claim 1 wherein the complex is N-(2-acetamido)-iminodiacetato(-trans,R,R-DACH)Pt(II).

44. A platinum complex of claim 1 having the formula:

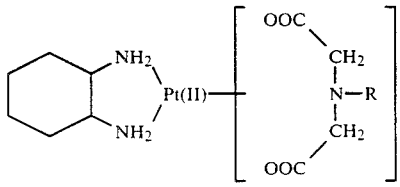

wherein R is hydrogen, phenyl, 2-acetamido, methyl, 2-hydroxyethyl or benzyl.

45. A pharmaceutical composition in unit dosage form suitable for administration to an animal afflicted with tumor cells sensitive to a platinum complex of claim 1 comprising a therapeutically anti-tumor effective amount of said platinum complex and a pharmaceutically acceptable carrier therefor.

46. The composition of claim 45 wherein said platinum complex has the formula:

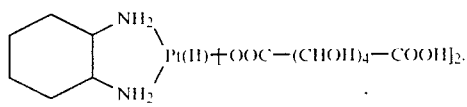

[bis-monosaccharato]

47. The composition of claim 45 wherein said platinum complex has the formula:

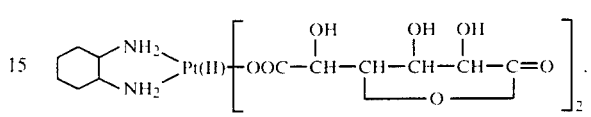

[bis-saccharato 1,4 lactone]

48. The composition of claim 45 wherein said platinum complex has the formula:

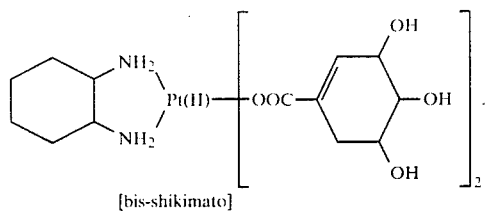

[bis-shikimato]

49. The composition of claim 45 wherein said platinum complex has the formula:

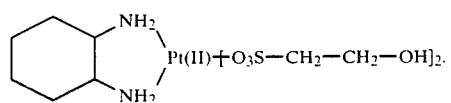

[bis-isethionato]

50. The composition of claim 45 wherein said platinum complex has the formula:

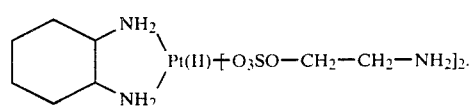

[bis-2-aminoethylsulfato]

51. The composition of claim 45 wherein said platinum complex has the formula:

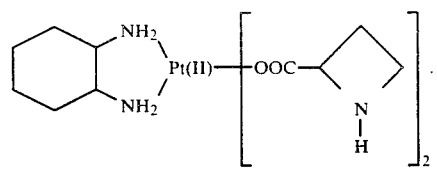

[bis-azetidinecarboxylato]

52. The composition of claim 45 wherein said platinum complex has the formula:

[bis-prolinato]

53. The composition of claim 45 wherein said platinum complex has the formula:

[bis-hydroxyprolinato]

54. The composition of claim 45 wherein said platinum complex has the formula:

[bis-pipecolinato]

55. The composition of claim 45 wherein said platinum complex has the formula:

[Iminodiacetato]

56. The composition of claim 45 wherein said platinum complex has the formula:

[isocitratolactone]

57. The composition of claim 45 wherein said platinum complex has the formula:

[furanedicarboxylate]

58. The composition of claim 45 wherein said platinum complex has the formula:

[cyclopropanedicarboxylato-]

59. The composition of claim 45 wherein said platinum complex has the formula:

[isocitratomonoethylester]

60. The composition of claim 45 wherein said platinum complex has the formula:

(bis-cyclopropanecarboxylato)

61. The composition of claim 45 wherein said platinum complex has the formula:

(bis-cyclobutanecarboxylato)

62. The composition of claim 45 wherein said platinum complex has the formula:

(bis-cyclopentanecarboxylato)

63. The composition of claim 45 wherein said platinum complex has the formula:

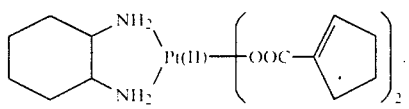

(bis-cyclopentenecarboxylato)

64. The composition of claim 45 wherein said platinum complex has the formula:

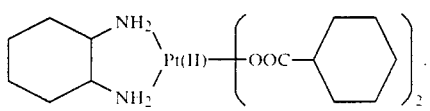

(bis-cyclohexanecarboxylato)

65. The composition of claim 45 wherein said platinum complex has the formula:

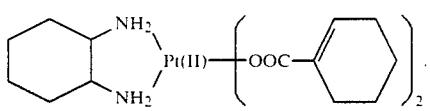

(bis-cyclohexenecarboxylato)

66. The composition of claim 45 wherein said platinum complex has the formula:

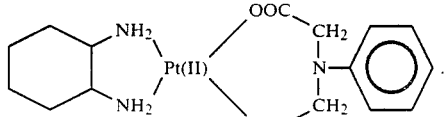

(N—phenyliminodiacetato)

67. The composition of claim 45 wherein said platinum complex has the formula:

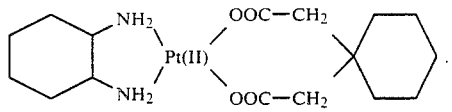

(cyclohexane-1,1-diacetato)

68. The composition of claim 45 wherein said platinum complex has the formula:

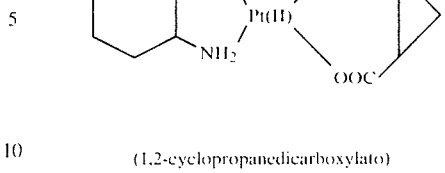

(1,2-cyclopropanedicarboxylato)

69. The composition of claim 45 wherein said platinum complex has the formula:

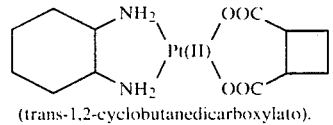

(trans-1,2-cyclobutanedicarboxylato).

70. The composition of claim 45 wherein said platinum complex has the formula:

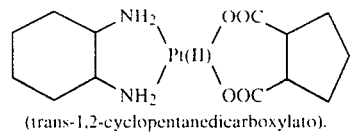

(trans-1,2-cyclopentanedicarboxylato).

71. The composition of claim 45 wherein said platinum complex has the formula:

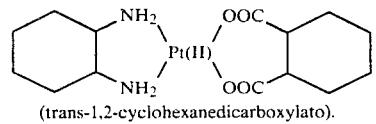

(trans-1,2-cyclohexanedicarboxylato).

72. The composition of claim 45 wherein said platinum complex has the formula:

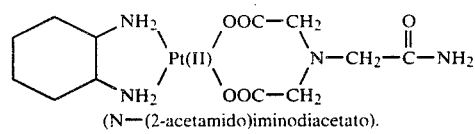

(N—(2-acetamido)iminodiacetato).

73. The composition of claim 45 wherein said platinum complex has the formula:

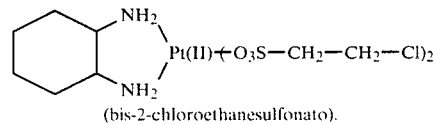

(bis-2-chloroethanesulfonato).

74. The composition of claim 45 wherein said platinum complex has the formula:

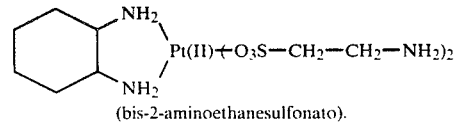

(bis-2-aminoethanesulfonato).

75. The composition of claim 45 wherein said platinum complex has the formula:

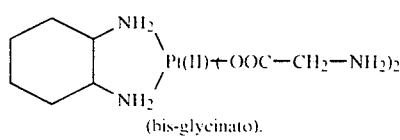

(bis-glycinato).

76. The composition of claim 45 wherein said platinum complex has the formula:

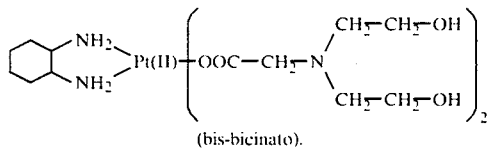

(bis-bicinato).

77. The composition of claim 45 wherein said platinum complex has the formula:

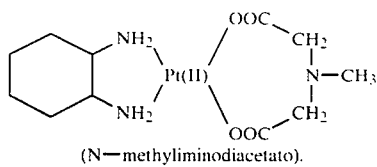

(N—methyliminodiacetato).

78. The composition of claim 45 wherein said platinum complex has the formula:

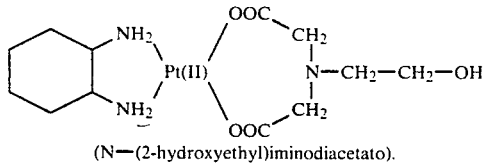

(N—(2-hydroxyethyl)iminodiacetato).

79. The composition of claim 45 wherein said platinum complex has the formula:

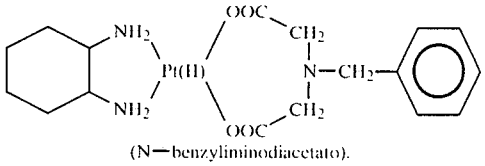

(N—benzyliminodiacetato).

80. The composition of claim 45 wherein said platinum complex has the formula:

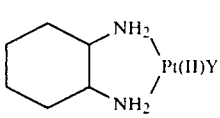

wherein Y is iminodiacetate, N-methyliminodiacetate, N-(2-hydroxyethyl)-iminodiacetate, N-phenyliminodiacetate or N-benzyliminodiacetate.

81. The composition of claim 80 wherein said complex is trans-R,R-DACH-Pt(II).

82. The composition of claim 81 wherein said platinum complex is mono-iminodiacetato-(trans-R,R-DACH)Pt(II) and aqueous complexes thereof.

83. The composition of claim 81 wherein said platinum complex is mono-N-methyliminodiacetato-(trans-R,R,-DACH)Pt(II) and aqueous complexes thereof.

84. The composition of claim 81 wherein said platinum complex is mono-N-hydroxyethyliminodiacetato-(trans-R,R-DACH)Pt(II) and aqueous complexes thereof.

85. The composition of claim 81 wherein said platinum complex is mono-N-phenyliminodiacetato-(trans-R,R-DACH)Pt(II) and aqueous complexes thereof.

86. The composition of claim 81 wherein said platinum complex is mono-N-benzyliminodiacetato-(trans-R,R-DACH)Pt(II) and aqueous complexes thereof.

* * * * *